United States Patent
Pugia et al.

(10) Patent No.: US 8,017,573 B2
(45) Date of Patent: Sep. 13, 2011

(54) ADIPONECTIN RECEPTOR FRAGMENTS AND METHODS OF USE

(75) Inventors: Michael J. Pugia, Granger, IN (US); Rui Ma, Mishawaka, IN (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 306 days.

(21) Appl. No.: 12/169,983

(22) Filed: Jul. 9, 2008

(65) Prior Publication Data
US 2009/0143275 A1  Jun. 4, 2009

Related U.S. Application Data

(60) Provisional application No. 60/991,328, filed on Nov. 30, 2007.

(51) Int. Cl.
*A61K 38/17* (2006.01)
(52) U.S. Cl. ........... 514/6.7; 514/6.9; 514/7.3; 514/21.3
(58) Field of Classification Search .................. None
See application file for complete search history.

(56) References Cited

U.S. PATENT DOCUMENTS

| | | | |
|---|---|---|---|
| 4,816,567 A | 3/1989 | Cabilly et al. | |
| 5,242,828 A | 9/1993 | Bergstrom et al. | |
| 5,719,060 A | 2/1998 | Hutchens et al. | |
| 5,831,012 A | 11/1998 | Nilsson et al. | |
| 6,124,137 A | 9/2000 | Hutchens et al. | |
| 6,225,047 B1 | 5/2001 | Hutchens et al. | |
| 6,329,209 B1 | 12/2001 | Wagner et al. | |
| 6,461,821 B1 | 10/2002 | Matsuzawa et al. | |
| 7,108,972 B2 | 9/2006 | Pena et al. | |
| 2003/0153013 A1 | 8/2003 | Huang | |
| 2004/0038428 A1 | 2/2004 | MacBeath et al. | |
| 2004/0241802 A1 | 12/2004 | Kadowaki et al. | |
| 2005/0032166 A1 | 2/2005 | Chen et al. | |
| 2005/0048565 A1 | 3/2005 | Tomita et al. | |
| 2005/0054005 A1 | 3/2005 | Ellis et al. | |
| 2007/0037226 A1 | 2/2007 | Golz et al. | |
| 2007/0053913 A1 | 3/2007 | Golz et al. | |
| 2010/0143958 A1 | 6/2010 | Pugia | |

FOREIGN PATENT DOCUMENTS

| | | |
|---|---|---|
| WO | WO99/51773 | 10/1999 |
| WO | WO00/56934 | 9/2000 |
| WO | WO01/12662 | 2/2001 |

(Continued)

OTHER PUBLICATIONS

Baughmann, et al., "Release of tumor necrosis factor by alveolar macrophages of patients with sarcoidosis" J. Lab. Clin. Med., 115: 36-42 (1990).

(Continued)

*Primary Examiner* — Jeffrey E Russel
(74) *Attorney, Agent, or Firm* — Kevin Stein

(57) ABSTRACT

Methods are disclosed of treating diabetes, abnormal adipocyte activity, and insulin resistance using C-terminal fragments of adiponectin receptor R1. Methods of causing the secretion of insulin in healthy and diabetic patients using C-terminal fragments of adiponectin receptor R1 are also disclosed. In addition, methods are disclosed of increasing the insulin levels in healthy patients using C-terminal fragments of adiponectin receptor R1. In addition, methods of treating abnormal adipocyte activity, treating metabolic syndrome, causing insulin secretion, increasing insulin levels, inhibiting insulin degradation enzyme, treating Alzheimer's disease, treating cardiovascular disease associated with adiponectin levels, inhibiting ADAM-17 enzyme, treating a condition associated with TNF-alpha, and treating a condition associated with HER2-neu are disclosed. Compositions, dosage forms, and kits are also disclosed.

28 Claims, 6 Drawing Sheets

FOREIGN PATENT DOCUMENTS

| WO | WO01/90304 | 11/2001 |
|---|---|---|
| WO | WO02/072149 | 9/2002 |
| WO | WO03/023008 | 3/2003 |
| WO | WO2004/022596 | 3/2004 |
| WO | WO2004/061108 | 7/2004 |
| WO | WO2004/063711 | 7/2004 |
| WO | WO2004/086040 | 10/2004 |
| WO | WO2005/031346 | 4/2005 |
| WO | WO2005/038457 | 4/2005 |
| WO | WO2005046734 | 5/2005 |
| WO | WO2006061555 | 12/2006 |
| WO | WO2007120311 | 10/2007 |

OTHER PUBLICATIONS

Bissonnette, et al., "Pulmonary Inflammation and Fibrosis in a Murine Model of Asbestosis and Silicosis" Inflammation, 13: 329-339 (1989).
Brutlag, et al., "Improved sensitivity of biological sequence database searches" Comp. App. Biosci., 6:3 237-245, 1990.
Elliot, et al., "TNFz Blockade in Rheumatoid Arthritis: Rationale, Clinical Outcomes and Mechanisms of Action" Int. J. Immunoparmac., V 17: 141-145 (1995).
Ferrai-Baliviera, et al., "Tumor Necrosis Factor Induces Adult Respiratory Distress Syndrome in Rats" Arch. Surg., 124: 1400-1405, 1989.
Grau, et al., "Tumor Necrosis Factor and Disases Severity in Children with Falciparum Malaria" New England Journal of Medicine, 320:1586-1591, 1989.
Hinshaw, et al., "Survival of Primates in LD100 Septic Shock Following Therapy with Antibody to Tumor Necrosis Factor (TNF)"; Circulatory Shock 30: 279-292, 1990.
Holler, et al., "Increased Serum Levels of Tumor Necrosis Factor a Precede Major Complications of Bone Marrow Transplantation" Blood, V. 75, N. 4, 1011-1016, 1990.
Johnson, et al., "Tumors Producing Human Tumor Necrosis Factor Induce Hypercalcemia and Osteoclastic Bone Resorption in Nude Mice" Endocrinology, 124:1424-1427, 1989.
Jones, et al., "Replacing the complementarity—determining regions in a human antibody with those from a mouse" Nature, 321: 522-525 (1986).
Kohler, et al., "Continuous cultures of fused cells secreting antibody of predefined specificity" Nature, 256: 495 (1975).
Marks, et al., "By-passing Immunization Human Antibodies from V-gene Libraries on Phage"; J. Mol. Biol., 222: 581-597 (1991).
Marks, et al., "By-passing Immunization: Building High Affinity Humand Antibodies by Chain Shuffling", Bio/Technology, 10: 779-783 (1992).
McCafferty, et al., "Phage antibodies: filamentous phage displaying antibody variable domains"; Nature, 348: 552-554 (1990).
Millar, et al., "Tumor Necrosis Factor in Bronchopulmonary Secretions of Patients with Adult Respiratory Distress Syndrome" Lancet, 2:712-714, 1989.
Parra, et al., "Tissue inhibitor of metalloproteinase-1 is increased in the saphenofemoral junction of patients with varices in the leg" J. Vasc. Surg., 28: 669-675 (1998).
Piguet, et al., "Requirement of tumour necrosis factor for development of silica-induced pulmonary fibrosis" Nature, 344:245-247, 1990.
Poli, et al., "The Effect of Cytokines and Pharmacologic Agents on Chronic HIV Infection" AIDS Research and Human Retrovirus, 8:2, 191-197 (1992).
Presta, "Antibody Engineering", Current Opinion in Structural Biology, 2: 593-596 (1992).
Reichmann, et al., "Reshaping human antibodies for therapy" Nature, 332: 323-329 (1988).
Rongen, et al., "Liposomes and immunoassays"; Journal of Immunological Methods, 204: 105-133 (1997).
Self, et al., "Advances in Immunoassay Technology" Current Opinion in Biotechnology, 7: 60-65 (1996).
Stewart, et al. "Solid Phase Peptide Synthesis" p. 91, 1984.
Tracey, et al., "Anti-cachectin/TNF monoclonal antibodies prevent septic shock during lethal bacteraemia" Nature, 330:662-664, 1987.
Yamauchi, T., et al., 'The fat-derived hormone adiponectin reverses insulin resistance associated with both lipoatrophy and obesity', Nature Medicine, V 7(8): 941-946, Aug. 2001.
Altschul, et al., 'Basic Local Alignment Search Tool', J. Mol. Biol., 215:403-410, 1990.
Avis, K.E., "Parenteral Preparations" Chapter 85, 1518-1677.
Bao, J., "Capillary electrophoretic immunoassays" Journal of Chromatography B., 699: 463-480 (1997).
Bertolini, et.al., "Stimulation of bone resorption and inhibition of bone formation in vitro by human tumour necrosis factors" Nature, 319:516-518, 1986.
Carpino, L.A., "1-Hydroxy-7-azabenzotriazole. An efficient peptide coupling additive," J. Am. Chem. Soc. 115 :4397-4398 (1993).
Clackson, et al., "Making anitbody fragments using phage display libraries" Nature, 352: 624-628 (1991).
Deen, D., 'Metabolic Syndrome: Time for Action', American Family Physician, 69(12), 2875-2882, 2004.
Dezube, et al., "Pentoxifylline and wellbeing in patients with cancer"; Lancet, 335:662, 1990.
Duh, et al., "Tumor necrosis factor a activates human immunodeficiency virus type 1 through induction of nuclear factor binding to the NF kB sites in the long terminal repeat"; Proc. Nat. Acad. Sci., 86: 5974-5978 (1989).
Folks, et al., "Tumor necrosis factor a induces expression of human immunodeficiency virus in a chronically infected T-cell clone" Proc. Nat. Acad. Sci., 86: 2365-2368 (1989).
Gish, W., et al., 'Identification of protein coding regions by database similarity search', Nature Genetics, vol. 3, 266-272, Mar. 1993.
Greene, T.W., et al., Protective Groups in Organic Synthesis, 2nd Ed., Wiley & Sons (1991).
Gorden, et al., "The clinical uses of leptin" Current Opinion in Pharmacology, 3: 655-659 (2003).
Higgins, et al., 'Using CLUSTAL for Multiple Sequence Alignments', Methods in Enzymol, 266:383-402, 1996.
Hodneland, C.D., et al, "Selective immobilization of proteins to self-assembled monolayers presenting active site-directed capture ligands" Proc. Natl. Acad. Sci., 99:8 5048-5052 (2002).
Huse, et al., "Generation of a large cominatorial library of the immunoglobulin repertoire in Phage Lamda" Science, 246: 1275-1281 (1989).
Kohler, et al., "Derivation of specific antibody-producing tissue culture and tumor lines by cell fusion" Eur. J. Immunol., 6: 511-519 (1976).
Lefkowitz, R.J., 'Variations on a theme', Nature, 351, 353-354, 1991.
Merrifield, R.B., "Solid Phase Peptide Synthesis. I. The Synthesis of a Tetrapeptide" J. Am. Chem. Soc., 85 (14): 2149-2154 (1963).
McFarlane, S. I., et.al., 'Insulin Resistance and Cardiovascular Disease', 86 (2), Downloaded from jcem.endojournals.org on Jun. 20, 2008, 6 pages.
Monte, et al., "Productive Human Immunodeficiency Virus-1 Infection of Megakaryocytic Cells is Enhanced by Tumor Necrosis Factor a" Blood, 79:10, 2670 (1992).
Morrison, et al., "Chimeric human antibody molecules: Mouse anitgen-binding domains with human constant region domains" Proc. Natl. Acad. Sci., 81: 6851-6855 (1984)
Peacock, W.F., "The B-type natriuretic peptide assay: A rapid test for heart failure" Cleveland Clinic Journal of Medicine, 69(3): 243-251 (2002).
Pearson, et al., 'Improved tools for biological sequence comparison', Proc. Natl. Acad. Sci., 85: 2444-2448, 1988.
Poli, et al., "Tumor necrosis factor a functions in an autocrine manner in the induction of human immunodeficiency virus expression" Proc. Natl. Acad. Sci., 87:782-784, 1990.
Pugia, et al., "Pathophysiology and diagnostic value of urinary trypsin inhibitors" Clin. Chem Lab Med, 43(1): 1-16, 2005.
Rudnic, et al, "Oral Solid Dosage Forms" Chapter 45, p. 858, The Remington: The Science and Practice of Pharmacy, 20th ed.; Lippincott Williams and Wilkins: Philadelphia, PA, 2000.
Schmalzing, et al., "Capillary electrophoresis based immunoassays: A critical review", Electrophoresis, 18: 2184-2193 (1997).

Tietge, U.J.F., et al., 'Elevated circulating adinopenctin levels in live cirrhosis are associated with reduced liver function and altered hepatic hemodynamics', Am. J. Physiol. Endocrinol. Metab, 287 (1): E82-E89, 2004.

Thompson, et al., 'Clustal W: improving the sensitivity of progressive multiple sequence alignment through sequence weighting, position-specific gap penalties and weight matrix choice', Nucleic Acids Res., 22:22 4673-4680, 1994.

Tsuchida, A., et al., 'Nuclear Receptors as Targets for Drug Development: Molecular Mechanisms for Regulation of Obesity and Insulin Resistance by Peroxisome Proliferator-Activated Receptor γ, CREB-Binding Protein, and Adiponectin', J. Pharmacol. Sci., 97:164-170, 2005.

von Dullemen, et al., "Treatmetn for Crohn's Disease with Anti-Tumor Necrosis Factor Chimeric Monoclonal Antibody (cA2)" Gastroenterology, 109: 129-135, (1995).

Waterhouse, et al., "Combinatorial infection and in vivo recombination: a strategy for making large phage antibody repertoires" Nucleic Acids Research, 21:9 2265-2266 (1993).

Yamauchi, T., et al., 'Adiponectin stimulates glucose utilization and fatty-acid oxidation by activating AMP-activated protein kinase', Nature Medicine, 8:11, 1288-1295, 2002.

Yamauchi, T., et al., "Globular Adiponectin Protected ob/ob Mice from Diabetes and ApoE-deficient Mice from Atherosclerosis*" The Journal of Biological Chemistry, V.278, N.4, 2461-2468, 2003.

Yamauchi, et al., Cloning of adiponectin receptors that mediate antidiabetic metabolic effects Nature, 423: 762-769, 2003.

Xiao, et al., "Proteomic patterns: their potential for disease diagnosis"; Mol Cell Endocrinol., 230 (1-2): 95-106, 2005.

Xu, A., et al., 'The fat-derived hormone adiponectin alleviates alcoholic and nonalcoholic fatty liver diseases in mice.' Journal of Clinical Investigation, 112:1, 91-100, Jul. 2003.

International Search Report and Written Opinion of International Application No. PCT/US2008/069500 mailed on Dec. 12, 2008.

International Preliminary Report on Patentability of International Application No. PCT/US2008/069500 mailed on Jun. 1, 2010.

SEQUENCE LISTING

```
<160> NUMBER OF SEQ ID NOS: 8

<210> SEQ ID NO 1
<211> LENGTH: 32
<212> TYPE: PRT
<213> ORGANISM: Homo Sapiens

<400> SEQUENCE: 1

Val Val Ala Ala Ala Phe Val His Phe Tyr Gly Val Ser Asn Leu Gln
1               5                   10                  15

Glu Phe Arg Tyr Gly Leu Glu Gly Gly Cys Thr Asp Asp Thr Leu Leu
                20                  25                  30

<210> SEQ ID NO 2
<211> LENGTH: 30
<212> TYPE: PRT
<213> ORGANISM: Homo Sapiens

<400> SEQUENCE: 2
```

```
His Val Leu Val Val Ala Ala Ala Phe Val His Phe Tyr Gly Val Ser
1               5                   10                  15

Asn Leu Gln Glu Phe Arg Tyr Gly Leu Glu Gly Gly Cys Thr
                20                  25                  30

<210> SEQ ID NO 3
<211> LENGTH: 2100
<212> TYPE: DNA
<213> ORGANISM: Homo Sapiens

<400> SEQUENCE: 3
ggcgctgaag atcggggccg ctcggccgca ggccgcctcc agcgccgcgg gatgtagcgc      60
gggggaccgc ggccccccagc agagcccgcc tgcccggctt gtctaccatc agagggagat    120
ctctgccccc tggggctgag agaccccaac ctttccccaa gctgaagctg cagggtattg    180
aggtaccagc cagatgtctt cccacaaagg atctgtggtg cacaggggga atggggctcc    240
tgccagtaac agggaagctg acacggtgga actggctgaa ctgggacccc tgctagaaga    300
gaagggcaaa cgggtaatcg ccaacccacc caaagctgaa gagagcaaa catgcccagt      360 gccccaggaa gaagaggagg aggtgcgggt actgacactt cccctgcaag cccaccacgc    420
catggagaag atggaagagt ttgtgtacaa ggtctgggag ggacgttgga gggtcatccc    480
atatgatgtg ctccctgact ggctaaagga caacgactat ctgctacatg gtcatagacc    540
tcccatgccc tcctttcggg cttgcttcaa gagcatcttc cgcattcata cagaaactgg    600
caacatctgg acccatctgc ttggtttcgt gctgtttctc tttttgggaa tcttgaccat    660
gctcagacca aatatgtact tcatggcccc tctacaggag aaggtggttt ttgggatgtt    720 cttttttgggt gcagtgctct gcctcagctt ctcctggctc tttcacaccg tctattgtca    780
ttcagagaaa gtctctcgga cttttttccaa actggactat tcagggattg ctcttctaat    840
tatggggagc tttgtcccct ggctctatta ttccttctac tgctccccac agccacggct    900
catctacctc tccatcgtct gtgtcctggg catttctgcc atcattgtgg cgcagtggga    960
ccggtttgcc actcctaagc accgcagac aagagcaggc gtgttcctgg acttggcttt   1020
gagtggcgtc gtgcccacca tgcactttac tatcgctgag ggctttgtca aggccaccac   1080
agtgggccag atgggctggt tcttcctcat ggctgtgatg tacatcactg gagctggcct   1140
ttatgctgct cgaattcctg agcgcttctt tcctggaaaa tttgacatat ggttccagtc   1200
tcatcagatt ttccatgtcc tggtggtggc agcagccttt gtccacttct atggagtctc   1260
caaccttcag gaattccgtt acggcctaga aggcggctgt actgatgaca cccttctctg   1320
agccttccca cctgcggggt ggaggaggaa cttcccaagt gcttttaaaa ataacttctt   1380
tgctgaagtg agaggaagag tctgagttgt ctgtttctag aagaaacctc ttagagaatt   1440
cagtaccaac caagcttcag cccactttca cacccactgg gcaataaact ttccatttcc   1500
attctcctag ctggggatgg gcatggtca aacttagcca tccctcctc agcaaggcat    1560 ctaccggccc ctcacagaga cagtactttg aaactcatgt tgagatttta ccctctcctc   1620
caaccatttt gggaaaatta tggactggga ctcttcagaa attctgtctt ttcttctgga   1680
agaaaatgtc cctcccttac ccccatcctt aactttgtat cctggcttat aacaggccat   1740
ccatttttgt agcacacttt tcaaaaacaa ttatatacc tggtcccatc tttctagggc    1800
ctggatctgc ttatagagca ggaagaataa agccaccaac ttttacctag cccggctaat   1860
catggaagtg tgtccaggct tcaagtaact tgagttttaa ttttttttttt ttcttggcag   1920 agtaatgtaa aatttaaatg gggaaagata tttaatattt aatactaagc tttaaaaaga   1980
```
aacctgctat cattgctatg tatcttgatg caaagactat gatgttaata aaagaaagta  2040
cagaagagac ttggcattca aagatttcaa aaaaaaaaaa aaaaaaaaaa aaaaaaaaaa  2100

<210> SEQ ID NO 4
<211> LENGTH: 375
<212> TYPE: PRT
<213> ORGANISM: Homo Sapiens

<400> SEQUENCE: 4

Met Ser Ser His Lys Gly Ser Val Val Ala Gln Gly Asn Gly Ala Pro
1               5                   10                  15

Ala Ser Asn Arg Glu Ala Asp Thr Val Glu Leu Ala Glu Leu Gly Pro
            20                  25                  30

Leu Leu Glu Glu Lys Gly Lys Arg Val Ile Ala Asn Pro Pro Lys Ala
        35                  40                  45

Glu Glu Glu Gln Thr Cys Pro Val Pro Gln Glu Glu Glu Glu Glu Val
    50                  55                  60

Arg Val Leu Thr Leu Pro Leu Gln Ala His His Ala Met Glu Lys Met
65                  70                  75                  80

Glu Glu Phe Val Tyr Lys Val Trp Glu Gly Arg Trp Arg Val Ile Pro
                85                  90                  95

Tyr Asp Val Leu Pro Asp Trp Leu Lys Asp Asn Asp Tyr Leu Leu His
            100                 105                 110

Gly His Arg Pro Pro Met Pro Ser Phe Arg Ala Cys Phe Lys Ser Ile
        115                 120                 125

Phe Arg Ile His Thr Glu Thr Gly Asn Ile Trp Thr His Leu Leu Gly
    130                 135                 140

Phe Val Leu Phe Leu Phe Leu Gly Ile Leu Thr Met Leu Arg Pro Asn
145                 150                 155                 160

Met Tyr Phe Met Ala Pro Leu Gln Glu Lys Val Val Phe Gly Met Phe
                165                 170                 175

Phe Leu Gly Ala Val Leu Cys Leu Ser Phe Ser Trp Leu Phe His Thr
            180                 185                 190

Val Tyr Cys His Ser Glu Lys Val Ser Arg Thr Phe Ser Lys Leu Asp
        195                 200                 205

Tyr Ser Gly Ile Ala Leu Leu Ile Met Gly Ser Phe Val Pro Trp Leu
    210                 215                 220

Tyr Tyr Ser Phe Tyr Cys Ser Pro Gln Pro Arg Leu Ile Tyr Leu Ser
225                 230                 235                 240

Ile Val Cys Val Leu Gly Ile Ser Ala Ile Ile Val Ala Gln Trp Asp
                245                 250                 255

Arg Phe Ala Thr Pro Lys His Arg Gln Thr Arg Ala Gly Val Phe Leu
            260                 265                 270

Gly Leu Gly Leu Ser Gly Val Val Pro Thr Met His Phe Thr Ile Ala
        275                 280                 285

Glu Gly Phe Val Lys Ala Thr Thr Val Gly Gln Met Gly Trp Phe Phe
    290                 295                 300

Leu Met Ala Val Met Tyr Ile Thr Gly Ala Gly Leu Tyr Ala Ala Arg
305                 310                 315                 320

Ile Pro Glu Arg Phe Phe Pro Gly Lys Phe Asp Ile Trp Phe Gln Ser
                325                 330                 335

His Gln Ile Phe His Val Leu Val Ala Ala Ala Phe Val His Phe Phe
            340                 345                 350

Tyr Gly Val Ser Asn Leu Gln Glu Phe Arg Tyr Gly Leu Glu Gly Gly

```
                         355                 360                 365

Cys Thr Asp Asp Thr Leu Leu
    370                 375

<210> SEQ ID NO 5
<211> LENGTH: 25
<212> TYPE: PRT
<213> ORGANISM: Artificial Sequence
<220> FEATURE:
<223> OTHER INFORMATION: Synthetic construct

<400> SEQUENCE: 5

His Phe Tyr Gly Val Ser Asn Leu Gln Glu Phe Arg Tyr Gly Leu Glu
1               5                   10                  15

Gly Gly Cys Thr Asp Asp Thr Leu Leu
            20                  25

<210> SEQ ID NO 6
<211> LENGTH: 10
<212> TYPE: PRT
<213> ORGANISM: Artificial Sequence
<220> FEATURE:
<223> OTHER INFORMATION: Synthetic construct

<400> SEQUENCE: 6

Val Val Ala Ala Ala Phe Val His Phe Tyr
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic construct

<400> SEQUENCE: 7

His Phe Tyr Gly Val Ser Asn Leu Gln Glu Phe Arg
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Synthetic construct

<400> SEQUENCE: 8

Ser Gly Cys Thr Asp Asp Thr Leu Leu
1               5
```

ADIPONECTIN RECEPTOR FRAGMENTS AND METHODS OF USE

CROSS REFERENCE TO RELATED APPLICATIONS

This application claims the benefit of U.S. Application No. 60/991,328, filed Nov. 30, 2007, the entire disclosure of which is herein incorporated by reference. This application is also related to:

(1) U.S. application Ser. No. 10/572,882, which is the national stage entry of PCT/EP04/10383 filed Sep. 16, 2004;
(2) U.S. application Ser. No. 10/572,883, which is the national stage entry of PCT/EP04/10384 filed Sep. 16, 2004;
(3) U.S. application Ser. No. 60/748,305 filed Dec. 7, 2005; and
(4) WO 2007/120,311 filed Dec. 4, 2006;

the entire disclosures of which are incorporated herein by reference.

FIELD OF THE INVENTION

The present invention generally relates to adiponectin receptor fragments. More particularly, the invention relates to methods of using adiponectin receptor fragments and compositions, dosage forms, and kits comprising adiponectin receptor fragments.

BACKGROUND OF THE INVENTION

Adiponectin Receptor 1 (ADIPOR1) is a seven transmembrane G protein coupled receptor (GPCR). See, for example, WO 01/012662 and WO 01/090304. Many medically significant biological processes are mediated by signal transduction pathways that involve G-proteins [Lefkowitz, Nature 351, 353-354 (1991)]. Certain extra cellular messengers (ECM), which are peptide fragments from the C-terminal of ADIPOR1, have diagnostic value in human blood. Their usefulness was confirmed using a polyclonal antibody with a mass measuring SELDI-TOF immuno-affinity method. Those inventions are the subject of related application WO 2007/120,311, which is incorporated herein by reference. In that work, a particular long peptide sequence of 32 amino acids (ECM32) was identified that was completely absent from all diabetic patients tested. Shorter peptide sequences were also found in blood but in both healthy and diabetic patients. The levels of the shorter peptide sequences were generally increased with disease state.

It was unexpectedly discovered that ECM32 (SEQ ID NO:1), a fragment of 3473 Da as confirmed by two separate monoclonal antibodies, when administered to patients, acted as an insulin-sensitizing agent. As such, this C-terminal fragment of ADIPOR1 may be a useful therapeutic agent to increase insulin secretion in patients in need thereof, including, but not limited to, patients suffering from diabetes, abnormal adipocyte activity, and insulin resistance. The methods, compositions, dosage forms, and kits of the present invention are directed toward these, as well as other, important ends.

SUMMARY OF THE INVENTION

It is has been unexpectedly discovered that certain C-terminal fragments of ADIPOR1 inhibit the enzymatic activity of ADAM-17 and insulin degradation enzyme (IDE) and thereby impact insulin levels and signal peptides impacted by these enzyme such as TNF-α. Accordingly, these C-terminal fragments are useful in the methods of treating diabetes, abnormal adipocyte activity, and insulin resistance, in methods of causing the secretion of insulin in healthy and diabetic patients, and in methods of increasing the insulin levels in healthy patients. Useful compositions, dosage forms, and kits have also been discovered.

The present invention is directed, in part, to methods of treating diabetes in a patient in need thereof, comprising the step of:

administering to said patient an effective amount of a peptide or a pharmaceutically-acceptable salt thereof, wherein said peptide has at least 75% identity with SEQ ID NO:1.

In other embodiments, the invention is directed to methods of treating abnormal adipocyte activity in a patient in need thereof, comprising the step of:

administering to said patient an effective amount of a peptide or a pharmaceutically-acceptable salt thereof;

wherein said peptide has at least 75% identity with SEQ ID NO:1.

In another embodiment, the invention is directed to methods of treating insulin resistance in a patient in need thereof, comprising the step of:

administering to said patient an effective amount of a peptide or a pharmaceutically-acceptable salt thereof;

wherein said peptide has at least 75% identity with SEQ ID NO:1.

In yet other embodiments, the invention is directed to methods of treating metabolic syndrome in a patient in need thereof, comprising the step of:

administering to said patient an effective amount of a peptide or a pharmaceutically-acceptable salt thereof;

wherein said peptide has at least 75% identity with SEQ ID NO:1.

In still other embodiments, the invention is directed to methods of causing insulin secretion in a patient, comprising the step of:

administering to said patient an effective amount of a peptide or a pharmaceutically-acceptable salt thereof;

wherein said peptide has at least 75% identity with SEQ ID NO:1.

In other embodiments, the invention is directed to methods of increasing insulin level in a patient, wherein said patient does not suffer from diabetes, comprising the step of:

administering to said patient an effective amount of a peptide or a pharmaceutically-acceptable salt thereof;

wherein said peptide has at least 75% identity with SEQ ID NO:1 or SEQ ID NO:2.

In yet other embodiments, the invention is directed to methods of inhibiting insulin degradation enzyme (IDE) in a patient, comprising the step of:

administering to said patient an effective amount of a peptide or a pharmaceutically-acceptable salt thereof;

wherein said peptide has at least 75% identity with at least one peptide selected from the group consisting of SEQ ID NO:1, SEQ ID NO:5, SEQ ID NO:6, SEQ ID NO:7, and SEQ ID NO:8.

In other embodiments, the invention is directed to methods of treating Alzheimer's disease in a patient, comprising the step of:

administering to said patient an effective amount of a peptide or a pharmaceutically-acceptable salt thereof;

wherein said peptide has at least 75% identity with at least one peptide selected from the group consisting of SEQ ID NO:1, SEQ ID NO:5, SEQ ID NO:6, SEQ ID NO:7, and SEQ ID NO:8.

In other embodiments, the invention is directed to methods of treating cardiovascular disease associated with adiponectin levels in a patient, comprising the step of:
administering to said patient an effective amount of a peptide or a pharmaceutically-acceptable salt thereof;
wherein said peptide has at least 75% identity with SEQ ID NO:1.

In yet other embodiments, the invention is directed to methods of inhibiting ADAM-17 enzyme in a patient, comprising the step of:
administering to said patient an effective amount of a peptide or a pharmaceutically-acceptable salt thereof;
wherein said peptide has at least 75% identity with SEQ ID NO:1.

In yet other embodiments, the invention is directed to methods of treating a condition associated with TNF-alpha in a patient, comprising the step of:
administering to said patient an effective amount of a peptide or a pharmaceutically-acceptable salt thereof;
wherein said peptide has at least 75% identity with SEQ ID NO:1.

In yet other embodiments, the invention is directed to methods of treating a condition associated with HER2 neu in a patient, comprising the step of:
administering to said patient an effective amount of a peptide or a pharmaceutically-acceptable salt thereof;
wherein said peptide has at least 75% identity with SEQ ID NO:1.

In another embodiment, the invention is directed to compositions, comprising:
a peptide or a pharmaceutically-acceptable salt thereof, wherein said peptide has at least 75% identity with at least one peptide selected from the group consisting of SEQ ID NO:1, SEQ ID NO:2, SEQ ID NO:5, SEQ ID NO:6, SEQ ID NO:7, and SEQ ID NO:8; and
at least one pharmaceutically-acceptable carrier.

In further embodiments, the invention is directed to compositions, comprising:
a purified peptide or a pharmaceutically-acceptable salt thereof, wherein said peptide has at least 75% identity with at least one peptide selected from the group consisting of SEQ ID NO:1, SEQ ID NO:2, SEQ ID NO:5, SEQ ID NO:6, SEQ ID NO:7, and SEQ ID NO:8;
optionally, at least one pharmaceutically-acceptable carrier.

In yet other embodiments, the invention is directed to injectable dosage forms, comprising:
the composition described herein; and
at least one solvent for said peptide.

In other embodiments, the invention is directed to inhalable dosage forms, comprising:
the composition described herein; and
at least one pharmaceutically-acceptable carrier for administration of said peptide via inhalation.

In another embodiment, the invention is directed to kits, comprising:
instructions for administering an injectable dosage form to a patient;
a container comprising a composition described herein;
a container comprising a pharmaceutically-acceptable solvent for said compositions.

In other embodiments, the invention is directed to kits, comprising:
instructions for administering an inhalable dosage form to a patient;
a container comprising a composition described herein;
a container comprising a pharmaceutically-acceptable solvent for said composition.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE INVENTION

Figure 1:
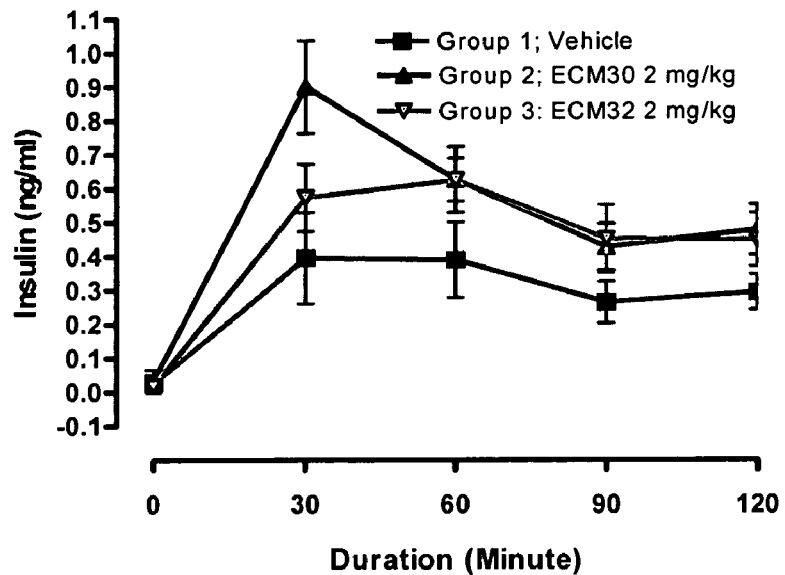
FIG. 1 is a plot of blood insulin levels in ng/ml as a function of time for a control, 2 mg/kg ECM30 in saline, and 2 mg/kg ECM32 in saline in normal patients.

As employed above and throughout the disclosure, the following terms, unless otherwise indicated, shall be understood to have the following meanings.

As used herein, the singular forms "a," "an," and "the" include the plural reference unless the context clearly indicates otherwise.

As used herein, the term "about," when referring to a measurable value such as an amount, a temporal duration, and the like, is meant to encompass variations of ±20%, preferably ±10%, more preferably ±5%, even more preferably ±1%, and yet even more preferably ±0.1% from the specified value, as such variations are appropriate to perform the disclosed methods and compositions.

As used herein, "effective amount" refers to an amount of the active ingredient as described herein that may be effective to prevent, reduce or eliminate the symptoms or condition and, with respect to this invention, including to treat diabetes, to treat abnormal adipocyte activity, to treat metabolic syndrome, to cause insulin secretion, to increase insulin levels, to inhibit insulin degradation enzyme, to treat Alzheimer's disease, to treat cardiovascular disease associated with adiponectin levels, to inhibit ADAM-17 enzyme, to treat a condition associated with TNF-alpha, and to treat a condition associated with HER2 neu. In general, the effective amount of the ADIPO R1 fragments of the invention, ranges from about 0.25 mg per kg patient weight to about 200 mg per kg patient weight, preferably about 25 mg per kg patient weight to about 175 mg per kg patient weight, and more preferably about 30 mg per kg patient weight to about 150 mg per kg patient weight (and all combinations and subcombinations therein).

As used herein, "treating" refers to the preventative, curative, and palliative treatment of a condition, and minimally requires a palliative effect.

As used herein, "pharmaceutically-acceptable" refers to those compounds, materials, compositions, and/or dosage forms that are, within the scope of sound medical judgment, suitable for contact with the tissues of human beings and animals without excessive toxicity, irritation, allergic response, or other problem complications commensurate with a reasonable benefit/risk ratio.

As used herein, "pharmaceutically-acceptable salts" refer to derivatives of the disclosed compounds wherein the parent compound is modified by making acid or base salts thereof, including acid addition salts and base addition salts. Examples of pharmaceutically-acceptable salts include, but are not limited to, mineral or organic acid salts of basic residues such as amines; alkali or organic salts of acidic residues such as carboxylic acids; and the like. The term "acid addition salt" refers to the corresponding salt derivative of a parent compound that has been prepared by the addition of an acid. The pharmaceutically-acceptable salts include the conventional salts or the quaternary ammonium salts of the parent compound formed, for example, from inorganic or organic acids. For example, such conventional salts include, but are not limited to, those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, adipic, alginic, aspartic, hydroxymaleic, phenylacetic, glutamic, benzoic, salicylic, sulfanilic, 2-acetoxybenzoic, fumaric, benzenesulfonic, toluenesulfonic, methanesulfonic, 2-napthalenesulfonic, ethane disulfonic, oxalic, isethionic, glucoheptanoic, glycerophosphoric, hemisulfanic, heptanoic, hexanoic, hydrochloric, hydrobromic, hydroiodic, 2-hydroxyethanesulfonic, 2-napthalenesulfonic, pectinic, phosphoric, sulfuric, 3-phenylpropionic, picric, pivalic, thiocyanic, p-toluenesulfonic, butyric, camphoric, camphorsulfonic, digluconic, cyclopentanepropionic, bisulfuric, dodecylsulfuric, ethanesulfonic, and undecanoic and the like. Thus, the term "base addition salt" refers to the corresponding salt derivative of a parent compound that has been prepared by the addition of a base. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. The pharmaceutically-acceptable salts include the conventional salts or the quaternary ammonium salts of the parent compound formed, for example, from inorganic or organic bases. For example, such conventional salts include, but are not limited to, those derived from inorganic bases such as lithium hydroxide, sodium hydroxide, potassium hydroxide, calcium hydroxide, magnesium hydroxide and ammonium hydroxide and the salts prepared from organic amines, such as methyl amine, ethyl amine, isopropyl amine, piperidine, piperizine, pyrrolidine, ethanolamine, morpholine, diazapine, ethylene diamine, pyridine, quinoline, quinuclidine, and the like.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As used herein, "dosage unit" refers to physically discrete units suited as unitary dosages for the particular patient to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

As used herein, "patient" refers to an animal, including a mammal, preferably a human.

As used herein, "healthy" refers to a patient that is not currently suffering from a condition or disease and includes a patient who is predisposed to suffering a condition. For example, a pre-diabetic patient would be considered a healthy patient for the purposes of this invention.

As used herein, "polypeptide," "peptide," and "protein fragment" are used interchangeably herein to refer to a polymer of amino acid residues. The terms includes amino acid polymers in which one or more amino acid residues is an artificial chemical mimetic of a corresponding naturally-occurring amino acid, as well as to naturally-occurring amino acid polymers and non-naturally-occurring amino acid polymers.

As used herein, "polynucleotide" means a polymeric form of nucleotides of at least about 10 bases or base pairs in length, either ribonucleotides or deoxyribonucleotides or a modified form thereof.

As used herein, "percent identity" refers the proportion of the polypeptide sequence that matches the reference polypeptide sequence and can be determined by comparing two optimally aligned sequences over a comparison window, wherein the polypeptide sequence in the comparison window can comprise additions, deletions (i.e., gaps), derivatization, and/or conservative amino acid substitutions as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Identity is evaluated using any of the variety of sequence comparison algorithms and programs known in the art. Such algorithms and programs include, but are by no means limited to, TBLASTN, BLASTP, FASTA, TFASTA, CLUSTALW, FASTDB, the entire disclosures of which are incorporated herein by reference. See, also, Pearson, et al., Proc. Natl. Acad. Sci. U.S.A., 85:2444-2448, 1988; Atlschul, et al., *J. Mol. Biol.*, 215:403410, 1990; Thompson, et al., *Nucleic*

*Acids Res.*, 22:4673-4680, 1994; Higgins, et al., *Meth. Enzymol.*, 266:383402, 1996; Altschul, et al, *Nature Genetics*, 3:266-272, 1993; Brutlag, et al., *Comp. App. Biosci.*, 6:237-44, 1990.

As used herein, "derivatization" refers to the process of chemically modifying by techniques such as ubiquitination, labeling, peglyation (i.e, derivatization with polyethylene glycol), and chemical insertion or substitution of amino acids, such as ornithine, which do not normally occur in human proteins.

As used herein, "conservative amino acid substitution" refers to the replacement of one amino acid with another having similar structure and/or chemical properties, such as the replacement of a leucine with an isoleucine or valine, an aspartate with a glutamate, or a threonine with a serine.

As used herein, "TACE" refers to tumor necrosis factor α-converting enzyme, and may be used interchangeably with "ADAM-17," which refers to disintegrin and metalloprotease domain 17, an enzyme that cleaves TNF and HERn.

As used herein, "diabetes" refers to diabetes mellitus, a chronic hyperglycemia due to defective insulin secretion and/or action. The World Health Organization recognizes three main forms of diabetes mellitus: type I, type II, and gestational diabetes. While all forms are due to the beta cells of the pancreas being unable to produce sufficient insulin to prevent hyperglycemia, the causes are different. Type I diabetes is usually due to autoimmune destruction of the pancreatic beta cells. Type II diabetes is characterized by insulin resistance in target tissues, which creates a need for abnormally high amounts of insulin and diabetes develops when the beta cells cannot meet this demand. Gestational diabetes is similar to type II diabetes in that it involves insulin resistance; the hormones of pregnancy can cause insulin resistance in women genetically predisposed to developing this condition. Gestational diabetes typically resolves with delivery of the child, however types I and II diabetes are chronic conditions. All types are treatable with insulin. Type I diabetes, in which insulin is not secreted by the pancreas, is directly treatable only with injected or inhaled insulin, although dietary and other lifestyle adjustments are part of management. Type II may be managed with a combination of dietary treatment, tablets and injections and, frequently, insulin supplementation.

Normal insulin sensitivity results when insulin cause fat cells to produce adiponectin. Adiponectin interacts with the adiponectin receptor 2 in the liver and the adiponectin receptor 1 in the muscle to stop glucose production and cause glycolysis and fatty acid oxidation. The adiponectin receptor 1 reacts with a cleaved form of adiponectin called globular adiponectin whereas adiponectin receptor 2 reacts to full length adiponectin.

Insulin resistance occurs when adipocytes become hypertropic and produce less adiponectin in response to insulin. In this state, the cells become more apoptotic and cell division slows. As a result, plasma adiponectin levels decrease. Insulin levels rise in an effort to cause cells to release more adiponectin. However, as the insulin resistance worsens more insulin and less adiponectin is produced. The lower level of adiponectin results in less glycolysis and fatty acid oxidation in muscle and prevents liver glucose production from stopping. As used herein, "insulin resistance" refers to a decrease in an individual in the biological action of insulin in vivo as assessed by the rate of disposal of glucose from the bloodstream (e.g., into insulin-sensitive tissue, such as muscle, fat, and liver).

As used herein, "metabolic syndrome" or "syndrome X" refers to a cluster of risk factors that is blamed for the excess cardiovascular disease morbidity among overweight and obese patients and patients with type II diabetes mellitus. Both the World Health Organization and National Cholesterol Education Program—Adult Treatment Patent (NCEP-ATP III) have set forth diagnostic criteria for metabolic syndrome (Darwin Deen, *American Family Physician*, 69(12): 2875-2882 (2004):

TABLE 1

Diagnostic Criteria for Metabolic Syndrome According to the WHO and the ATP III

| Component | WHO diagnostic criteria (insulin resistance* plus two of the following) | ATP III diagnostic criteria (three of the following) |
| --- | --- | --- |
| Abdominal/central obesity | Waist to hip ratio: >0.90 (men), >0.85 (women), or BMI > 30 kg per m² | Waist circumference: >102 cm (40 in) in men, >88 cm (35 in) in women |
| Hypertriglyceridemia | >=150 mg per dL (>=1.7 mmol per L) | >=150 mg per dL |
| Low HDL cholesterol | <35 mg per dL (<0.9 mmol per L) for men, <39 mg per dL (<1.0 mmol per L) for women | <40 mg per dL (<1.036 mmol per L) for men, <50 mg per dL (<1.295 mmol per L) for women |
| High blood pressure | >=140/90 mm Hg or documented use of antihypertensive therapy | >=130/85 mm Hg or documented use of antihypertensive therapy |
| High fasting glucose | Impaired glucose tolerance, impaired fasting glucose, insulin resistance, or diabetes | >=110 mg per dL (>=6.1 mmol per L)† |
| Microalbuminuria | Urinary albumin to creatinine ratio: 30 mg per g, or albumin excretion rate: 20 mcg per minute | |

WHO = World Health Organization;
ATP = Adult Treatment Panel;
BMI = body mass index;
HDL = high-density lipoprotein.
*Insulin resistance is identified by type 2 diabetes mellitus or impaired fasting glucose.

As used herein, "cardiovascular disease" refers to any disease that affects the heart and blood vessels, including diseases related to atherosclerosis (arterial disease) that can cause heart attacks and certain types of strokes.

As used herein, "condition associated with TNF-alpha" refers to any pathological condition or disease mediated by TNF-alpha converting enzyme (TACE) in a mammal.

Examples of such conditions and diseases include, but are not limited to: HIV; hepatitis; adult respiratory distress syndrome; bone-resorption diseases; chronic obstructive pulmonary diseases; chronic pulmonary inflammatory diseases; dermatitis; cystic fibrosis; septic shock; sepsis; endotoxic shock; hemodynamic shock; sepsis syndrome; post ischemic reperfusion injury; meningitis; psoriasis; fibrotic disease; cachexia; graft versus host disease (GVHD); graft rejection; auto-immune disease; rheumatoid spondylitis; arthritic conditions, such as rheumatoid arthritis, rheumatoid spondylitis and osteoarthritis; osteoporosis; inflammatory-bowel disease; Crohn's disease; ulcerative colitis; multiple sclerosis; systemic lupus erythrematosus; ENL in leprosy; radiation damage; asthma; type-I diabetes, and hyperoxic alveolar injury, and combinations thereof. Tracey, et al., 1987, *Nature* 330:662 664 and Hinshaw, et al., 1990, *Circ. Shock* 30:279 292 (endotoxic shock); Dezube, et al., 1990, *Lancet,* 335:662 (cachexia); Millar, et al., 1989, *Lancet* 2:712 714 and Ferrai-Baliviera, et al., 1989, *Arch. Surg.* 124:1400 1405 (adult respiratory distress syndrome); Bertolini, et al., 1986, *Nature* 319:516 518, Johnson, et al., 1989, *Endocrinology* 124:1424 1427, Holler, et al., 1990, *Blood* 75:1011 1016, and Grau, et al., 1989, *N. Engl. J. Med.* 320:1586 1591 (bone resorption diseases); Pignet, et al., 1990, *Nature,* 344:245 247, Bissonnette, et al., 1989, *Inflammation* 13:329 339 and Baughman, et al., 1990, *J. Lab. Clin. Med.* 115:36 42 (chronic pulmonary inflammatory diseases); Elliot, et al., 1995, *Int. J. Pharmac.* 17:141 145 (rheumatoid arthritis); von Dullemen, et al., 1995, *Gastroenterology,* 109:129 135 (Crohn's disease); Duh, et al., 1989, *Proc. Nat. Acad. Sci.* 86:5974 5978, Poll, et al., 1990, *Proc. Nat. Acad. Sci.* 87:782 785, Monto, et al., 1990, *Blood* 79:2670, Clouse, et al., 1989, *J. Immunol.* 142, 431 438, Poll, et al., 1992, *AIDS Res. Hum. Retrovirus,* 191 197, Poli, et al. 1990, *Proc. Natl. Acad. Sci.* 87:782 784, Folks, et al., 1989, *PNAS* 86:2365 2368 (HIV and opportunistic infections resulting from HIV).

As used herein, "condition associated with HER2-neu" refers to any pathological condition or disease mediated by human epidermal growth factor receptor 2 (HER2-neu) in a mammal, including tumor growth, especially in breast cancer.

The nucleotide sequence of ADIPOR1 is accessible in public databases by the accession number NM_015999 and is given in SEQ ID NO:3. The amino acid sequence of ADIPOR1 is depicted in SEQ ID NO:4. The adiponectin receptors, ADIPOR1 and ADIPOR2, serve as receptors for globular and full-length adiponectin and mediate increased AMPK and PPAR-alpha ligand activities, as well as fatty acid oxidation and glucose uptake by adiponectin [Yamauchi, et al., *Nature* 423: 762-769 (2003)]. Yamauchi, et al. [Yamauchi, et al., *Nature* 423: 762-769 (2003)] isolated cDNAs encoding ADIPOR1 and ADIPOR2 by expression cloning. The receptor ADIPOR1 is published in [Yamauchi, et al., *Nature* 423: 762-769 (2003)].

Accordingly, the present invention is directed, in part, to methods of treating diabetes in a patient in need thereof, comprising the step of:
administering to said patient an effective amount of a peptide or a pharmaceutically-acceptable salt thereof;
wherein said peptide has at least 75% identity with SEQ ID NO:1.

In other embodiments, the invention is directed to methods of treating abnormal adipocyte activity in a patient in need thereof, comprising the step of:
administering to said patient an effective amount of a peptide or a pharmaceutically-acceptable salt thereof;
wherein said peptide has at least 75% identity with SEQ ID NO:1.

In another embodiment, the invention is directed to methods of treating insulin resistance in a patient in need thereof, comprising the step of:
administering to said patient an effective amount of a peptide or a pharmaceutically-acceptable salt thereof;
wherein said peptide has at least 75% identity with SEQ ID NO:1.

In yet other embodiments, the invention is directed to methods of treating metabolic syndrome in a patient in need thereof, comprising the step of:
administering to said patient an effective amount of a peptide or a pharmaceutically-acceptable salt thereof;
wherein said peptide has at least 75% identity with SEQ ID NO:1.

In still other embodiments, the invention is directed to methods of causing insulin secretion in a patient, comprising the step of:
administering to said patient an effective amount of a peptide or a pharmaceutically-acceptable salt thereof;
wherein said peptide has at least 75% identity with SEQ ID NO:1.

In other embodiments, the invention is directed to methods of increasing insulin level in a patient, wherein said patient does not suffer from diabetes, comprising the step of:
administering to said patient an effective amount of a peptide or a pharmaceutically-acceptable salt thereof;
wherein said peptide has at least 75% identity with SEQ ID NO:1 or SEQ ID NO:2.

In certain embodiments of the invention, the patient suffers from type I or type II diabetes. In other embodiments of the invention, patient suffers from gestational diabetes.

In yet other embodiments, the invention is directed to methods of inhibiting insulin degradation enzyme (IDE) in a patient, comprising the step of:
administering to said patient an effective amount of a peptide or a pharmaceutically-acceptable salt thereof;
wherein said peptide has at least 75% identity with at least one peptide selected from the group consisting of SEQ ID NO:1, SEQ ID NO:5, SEQ ID NO:6, SEQ ID NO:7, and SEQ ID NO:8.

In other embodiments, the invention is directed to methods of treating Alzheimer's disease in a patient, comprising the step of:
administering to said patient an effective amount of a peptide or a pharmaceutically-acceptable salt thereof;
wherein said peptide has at least 75% identity with at least one peptide selected from the group consisting of SEQ ID NO:1, SEQ ID NO:5, SEQ ID NO:6, SEQ ID NO:7, and SEQ ID NO:8.

In other embodiments, the invention is directed to methods of treating cardiovascular disease associated with adiponectin levels in a patient, comprising the step of:
administering to said patient an effective amount of a peptide or a pharmaceutically-acceptable salt thereof;
wherein said peptide has at least 75% identity with at least one peptide selected from the group consisting of SEQ ID NO:1.

In yet other embodiments, the invention is directed to methods of inhibiting ADAM-17 enzyme in a patient, comprising the step of:
administering to said patient an effective amount of a peptide or a pharmaceutically-acceptable salt thereof;
wherein said peptide has at least 75% identity with SEQ ID NO:1.

Thus, SEQ ID NO:1 is useful as an anti-TNF alpha therapy and as an anti-HER2 neu therapy. Anti-TNF alpha therapy is important in treating inflammation and auto-immune diseases, such as lupus, rheumatoid arthritis, and type-1 diabetes. Anti-HER2 neu therapy is important in impacting tumor growth, especially in breast cancer.

In yet other embodiments, the invention is directed to methods of treating a condition associated with TNF-alpha in a patient, comprising the step of:

administering to said patient an effective amount of a peptide or a pharmaceutically-acceptable salt thereof;

wherein said peptide has at least 75% identity with SEQ ID NO:1.

In yet other embodiments, the invention is directed to methods of treating a condition associated with HER2 neu in a patient, comprising the step of:

administering to said patient an effective amount of a peptide or a pharmaceutically-acceptable salt thereof;

wherein said peptide has at least 75% identity with SEQ ID NO:1.

In certain instances, the C-terminal fragments of ADIPOR1 useful in the methods, compositions, dosage forms, and kits of the invention do not have the exact sequence as described herein, but is present as a variant form. For example, the C-terminal fragments of ADIPOR1 of the invention can substitute at least 5%, at least 10%, or even at least 25% of their amino acids without having a loss of function. Accordingly, at least some of the amino acids in the peptides of SEQ ID NO:1, SEQ ID NO:2, SEQ ID NO:5, SEQ ID NO:6, SEQ ID NO:7, and SEQ ID NO:8 can be substituted with other amino acids.

In certain embodiments of the invention, the peptide has at least 80% identity with SEQ ID NO:1, SEQ ID NO:2, SEQ ID NO:5, SEQ ID NO:6, SEQ ID NO:7, or SEQ ID NO:8, preferably, the peptide has at least 90% identity with SEQ ID NO:1, SEQ ID NO:2, SEQ ID NO:5, SEQ ID NO:6, SEQ ID NO:7, or SEQ ID NO:8, more preferably, the peptide has at least 95% identity with SEQ ID NO:1, SEQ ID NO:2, SEQ ID NO:5, SEQ ID NO:6, SEQ ID NO:7, or SEQ ID NO:8, yet even more preferably, the peptide has at least 97% identity with SEQ ID NO:1, SEQ ID NO:2, SEQ ID NO:5, SEQ ID NO:6, SEQ ID NO:7, or SEQ ID NO:8, even more preferably, the peptide has at least 98% identity with SEQ ID NO:1, SEQ ID NO:2, SEQ ID NO:5, SEQ ID NO:6, SEQ ID NO:7, or SEQ ID NO:8.

In certain embodiments, the methods are directed to treating patients suffering from diabetes. In certain embodiments, the methods are directed to treating patients suffering from abnormal adipocyte activity. In certain embodiments, the methods are directed to treating patients suffering from insulin resistance. In certain embodiments, the methods are directed to treating patients suffering from metabolic syndrome.

In certain embodiments of the invention, the peptide or pharmaceutically-acceptable salt thereof is administered via a parenteral route. In certain preferred embodiments, the peptide or pharmaceutically-acceptable salt thereof is administered via injection. In other preferred embodiments, the peptide or pharmaceutically-acceptable salt thereof is administered via infusion. In yet other preferred embodiments, the peptide or pharmaceutically-acceptable salt thereof is administered via inhalation.

In another embodiment, the invention is directed to compositions, comprising:

a peptide or a pharmaceutically-acceptable salt thereof, wherein said peptide has at least 75% identity with at least one peptide selected from the group consisting of SEQ ID NO:1, SEQ ID NO:2, SEQ ID NO:5, SEQ ID NO:6, SEQ ID NO:7, and SEQ ID NO:8; and at least one pharmaceutically-acceptable carrier.

In further embodiments, the invention is directed to compositions, comprising:

a purified peptide or a pharmaceutically-acceptable salt thereof, wherein said peptide has at least 75% identity with at least one peptide selected from the group consisting of SEQ ID NO:1, SEQ ID NO:2, SEQ ID NO:5, SEQ ID NO:6, SEQ ID NO:7, and SEQ ID NO:8;

optionally, at least one pharmaceutically-acceptable carrier.

In yet other embodiments, the invention is directed to injectable dosage forms, comprising:

the composition described herein; and at least one solvent for said peptide.

In other embodiments, the invention is directed to inhalable dosage forms, comprising:

the composition described herein; and at least one pharmaceutically-acceptable carrier for administration of said peptide via inhalation.

In another embodiment, the invention is directed to kits, comprising:

instructions for administering an injectable dosage form to a patient;

a container comprising a composition described herein;

a container comprising a pharmaceutically-acceptable solvent for said compositions.

In other embodiments, the invention is directed to kits, comprising:

instructions for administering an inhalable dosage form to a patient;

a container comprising a composition described herein;

a container comprising a pharmaceutically-acceptable solvent for said composition.

In certain embodiments of the invention, the composition is lyophilized.

A pharmaceutical composition of the invention is formulated to be compatible with its intended route of administration, which is preferably a parenteral route, especially intravenous (via injection or via infusion) or via inhalation. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents, such as benzyl alcohol or methyl parabens; antioxidants, such as ascorbic acid or sodium bisulfite; chelating agents, such as ethylenediaminetetraacetic acid; buffers, such as acetates, citrates, or phosphates, and agents for adjusting tonicity, such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate-buffered saline (PBS). In all cases, the composition must be sterile and should be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, a pharmaceutically-acceptable polyol like glycerol, propylene glycol, liquid polyethylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols, such as mannitol, sorbitol, and sodium chloride in the composition. Prolonged absorption of the injectable composition can be brought about by including in the composition an agent that delays absorption, for example, aluminum monostearate and gelatin. Sterile injectable solutions can be prepared by incorporating the active ingredient (i.e., the polypeptide) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the other required ingredients from those enumerated above. In the case of sterile powders for the preparation of sterile injectable solutions, the preferred methods of preparation are vacuum drying and freeze-drying, which yield a powder of the active ingredient plus and desired ingredients from a previously sterile-filtered solution thereof.

For administration via inhalation, the peptides are delivered in the form of an aerosol spray from a pressurized container or dispenser that contains a suitable propellant, e.g., a gas such as carbon dioxide, or a nebulizer.

It is especially advantageous to formulate the compositions in dosage unit form for ease of administration and uniformity of dosage. Dosage unit form, as used herein, refers to physically discrete units suited as unitary dosages for the patient to be treated; each unit containing a predetermined quantity of the peptide calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of the patients.

The pharmaceutical compositions can be included in a container, pack, or dispenser together with instructions for administration.

In certain embodiments of the invention, the compositions further comprise at least one pharmaceutically-acceptable carrier. In certain preferred embodiments, the pharmaceutically-acceptable carrier is sodium lactate. Other pharmaceutical carriers useful in the solutions and compositions useful in the practice of the present invention include, but are not limited to, proteins, peptides, amino acids, lipids, polymers, and carbohydrates (e.g., sugars, including monosaccharides, di-, tri-, terra-, and oligosaccharides; derivatized sugars such as alditols, aldonic acids, esterified sugars; and polysaccharides or sugar polymers), which may be present singly or in combination. Exemplary protein carriers include serum albumin such as human serum albumin (HSA), recombinant human albumin (rHA), gelatin, and casein. Representative amino acid/polypeptide components, which may also function in a buffering capacity, include alanine, glycine, arginine, betaine, histidine, glutamic acid, aspartic acid, cysteine, lysine, leucine, proline, isoleucine, valine, methionine, phenylalanine, and aspartame. Polyamino acids of the representative amino acids such as di-leucine and tri-leucine are also suitable for use with the present invention. Carbohydrate carriers suitable for use in the invention include, for example, monosaccharides such as fructose, maltose, galactose, glucose, D-mannose, and sorbose; disaccharides, such as lactose, sucrose, trehalose, cellobiose; polysaccharides, such as raffinose, melezitose, maltodextrins, dextrans, and starches; and alditols, such as mannitol, xylitol, maltitol, lactitol, xylitol sorbitol (glucitol), and myoinositol. Additionally, the solutions and compositions useful in the invention may include polymeric carriers such as polyvinylpyrrolidones, hydroxypropyl methylcellulose, methylcellulose, ethylcellulose, Ficolls (a polymeric sugar), dextran, dextrates (e.g., cyclodextrins, such as 2-hydroxypropyl-P-cyclodextrin, hydroxyethyl starch), polyethylene glycols, pectin, salts (e.g., sodium chloride), antioxidants, antistatic agents, surfactants (e.g., polysorbates such as "TWEEN 20" and "TWEEN 80", lecithin, oleic acid, benzalkonium chloride, and sorbitan esters), lipids (e.g., phospholipids, fatty acids), steroids (e.g., cholesterol), and chelating agents (e.g., EDTA). Other examples of pharmaceutical carriers and/or additives suitable for use in the solutions and compositions of the invention are listed in *Remington: The Science & Practice of Pharmacy,* 20th ed., Williams & Williams, (2000), and in the *Physician's Desk Reference,* 52nd ed., Medical Economics, Montvale, N.J. (1998), the disclosures of which are herein incorporated by reference.

In certain embodiments of the invention, the pharmaceutically-acceptable solvent for the peptides of SEQ ID NO:1, SEQ ID NO:2, SEQ ID NO:5, SEQ ID NO:6, SEQ ID NO:7, or SEQ ID NO:8 or a pharmaceutically-acceptable salt thereof is water, aqueous sodium chloride solution, aqueous potassium chloride solution, aqueous magnesium chloride hexahydrate solution, aqueous sodium acetate trihydrate solution, aqueous sodium gluconate solution, aqueous sodium hydroxide solution, aqueous dextrose solution, Lactated Ringer's solution, or a combination thereof. In certain embodiments of the invention, the pharmaceutically-acceptable solvent for the peptides of SEQ ID NO:1, SEQ ID NO:2, SEQ ID NO:5, SEQ ID NO:6, SEQ ID NO:7, or SEQ ID NO:8 or a pharmaceutically-acceptable salt thereof is aqueous alcohol, such as, for example, 20% ethanol.

In certain embodiments of the invention, the solution comprising the peptides of SEQ ID NO:1, SEQ ID NO:2, SEQ ID NO:5, SEQ ID NO:6, SEQ ID NO:7, or SEQ ID NO:8 or a pharmaceutically-acceptable salt thereof has a pH of about 3.5 to about 5.5. The solution may also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers.

In certain embodiments of the invention, the peptides of SEQ ID NO:1, SEQ ID NO:2, SEQ ID NO:5, SEQ ID NO:6, SEQ ID NO:7, or SEQ ID NO:8 and pharmaceutically-acceptable salts thereof or compositions comprising these peptides are lyophilized.

The various dosage forms are prepared in accordance with acceptable pharmaceutical procedures, such as described in *Remington: The Science and Practice of Pharmacy,* $20^{th}$ ed.; Gennaro, A. R., Ed.; Lippincott Williams & Wilkins: Philadelphia, Pa., (2000).

In addition, the compositions of the invention may further comprise a second active ingredient in addition to the peptides of SEQ ID NO:1, SEQ ID NO:2, SEQ ID NO:5, SEQ ID NO:6, SEQ ID NO:7, or SEQ ID NO:8 or its pharmaceutically acceptable salt, which is useful for the concurrent or synergistic treatment of diabetes, abnormal adipocyte activity, and insulin resistance. These compounds, and compositions thereof, may include additional compounds known to be useful for the treatment of diabetes, abnormal adipocyte activity, and insulin resistance. Suitable additional compounds include sulfonylureas, meglitinides, biguanides, thiazolidinediones, DPP-4 Inhibitors, alpha-glucosidase inhibitors, glucagons like-peptide (GLP-1)/exendin-4, and combinations thereof The peptides of SEQ ID NO:1, SEQ ID NO:2, SEQ ID NO:5, SEQ ID NO:6, SEQ ID NO:7, or SEQ ID NO:8 or its pharmaceutically acceptable salt of the invention may be prepared in a number of ways well known to those skilled in the art. The peptides of SEQ ID NO:1, SEQ ID NO:2, SEQ ID NO:5, SEQ ID NO:6, SEQ ID NO:7, or SEQ ID NO:8 and their pharmaceutically acceptable salts can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

The peptides useful in the invention may be prepared recombinantly or synthesized by conventional methods in liquid-phase or solid-phase, using manual or automated techniques. Suitable methods are described generally, for example, in:

Atherton, E. and Sheppard, R. C., *Solid Phase peptide synthesis: a practical approach*. Oxford, England: IRL Press (1989);

Stewart, J. M. and Young, J. D., *Solid phase peptide synthesis, 2nd edition*, Rockford: Pierce Chemical Company, 91 (1984);

R. B. Merrifield, "Solid Phase Peptide Synthesis. I. The Synthesis of a Tetrapeptide," *J. Am. Chem. Soc.* 85 (14): 2149-2154 (1963); and L. A. Carpino "1-Hydroxy-7-azabenzotriazole. An efficient peptide coupling additive," *J. Am. Chem. Soc.* 115 (10): 4397-4398 (1993);

which are incorporated herein by reference. Additionally, any portion of the amino acid sequence of the peptides can be altered during direct synthesis and/or combined using chemical methods with sequences with other proteins to produce a variant peptide.

Preferably, the peptides are prepared by conventional solid-phase peptide synthesis methodology. Standard synthesis protocols based on Fmoc chemistry may be used. After synthesis, the crude peptides are cleaved from the solid support and side-chain protecting groups are removed. The crude peptides can be purified, for example, by preparative high performance liquid chromatograpy, such as C18 reverse-phase HPLC. The purified peptide can be further desalted by HPLC and lyophilized to dry form. Preferable, the peptides are stored in sealed containers under nitrogen.

All forms of the peptides of SEQ ID NO:1, SEQ ID NO:2, SEQ ID NO:5, SEQ ID NO:6, SEQ ID NO:7, or SEQ ID NO:8, including free acid, free base, zwitterionic form, isomorphic crystalline forms, all chiral, enantiomeric, racemic forms, hydrates, solvates, salts and acid salt hydrates, are contemplated to be within the scope of the present invention. The free acid and the sodium, potassium, and calcium salts are the preferred forms.

The peptides of SEQ ID NO:1, SEQ ID NO:2, SEQ ID NO:5, SEQ ID NO:6, SEQ ID NO:7, or SEQ ID NO:8 of the invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl group. Other preferred protecting groups that may be employed in accordance with the present invention may be described in Greene, T. W. and Wuts, P. G. M., *Protective Groups in Organic Synthesis* 2d. Ed., Wiley & Sons, 1991.

Pharmaceutical kits useful in, for example, the treatment of diabetes, abnormal adipocyte activity, and insulin resistance, which comprise an effective amount of peptide of SEQ ID NO:1, SEQ ID NO:2, SEQ ID NO:5, SEQ ID NO:6, SEQ ID NO:7, or SEQ ID NO:8 or pharmaceutically-acceptable salts thereof in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL™ two-part container (available from Abbott Labs, Chicago, Ill.), as desired. Such kits may further include, if desired, one or more of various conventional pharmaceutical kit components, such as for example, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

The present invention is further defined in the following Examples, in which all parts and percentages are by weight, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

Synthesis of SEQ ID NO:1, SEQ ID NO:2, SEQ ID NO:5, SEQ ID NO:6, SEQ ID NO:7, and SEQ ID NO:8

The peptides of SEQ ID NO:1, SEQ ID NO:2, SEQ ID NO:5, SEQ ID NO:6, SEQ ID NO:7, and SEQ ID NO:8 were synthesized using conventional solid-phase peptide synthesis methodology:

| | | SEQ ID NO: 1 |
|---|---|---|
| (ECM32): | VVAAAFVHFYGVSNLQEFRYGLEGGCTDDTLL | |
| | | SEQ ID NO: 2 |
| (ECM30): | HVLVVAAAFVHFYGVSNLQEFRYGLEGGCT | |
| (ECM25): | HFYGVSNLQEFRYGLEGGCTDDTLL | SEQ ID NO: 5 |
| (ECM 10): | VVAAAFVHFY | SEQ ID NO: 6 |
| (ECM 12): | HFYGVSNLQEFR | SEQ ID NO: 7 |
| (ECM:9): | SGCTDDTLL | SEQ ID NO: 8 |

Standard synthesis protocols based on Fmoc chemistry were used. After synthesis, the crude peptides were cleaved from the solid support and side-chain protecting groups were removed. The crude peptides were purified by C18 reverse-phase HPLC using Varian SD-2 Instrument. The peptides were eluted with a gradient of Buffer B for 30 minutes (Buffer A: aqueous phase with 0.1% TFA, pH 2.5 and Buffer B: acetonitrile; flow rate 600 ml/min and detection at 230 mm). The purified peptide were further desalted by HPLC and lyophilized to dry form. The peptides were characterized by analytical HPLC analysis and mass spectrometry analysis, and then packed in sealed vials filled with nitrogen.

Example 2

Plasma Glucose and Insulin Testing in Normal Rats

Figure 2:
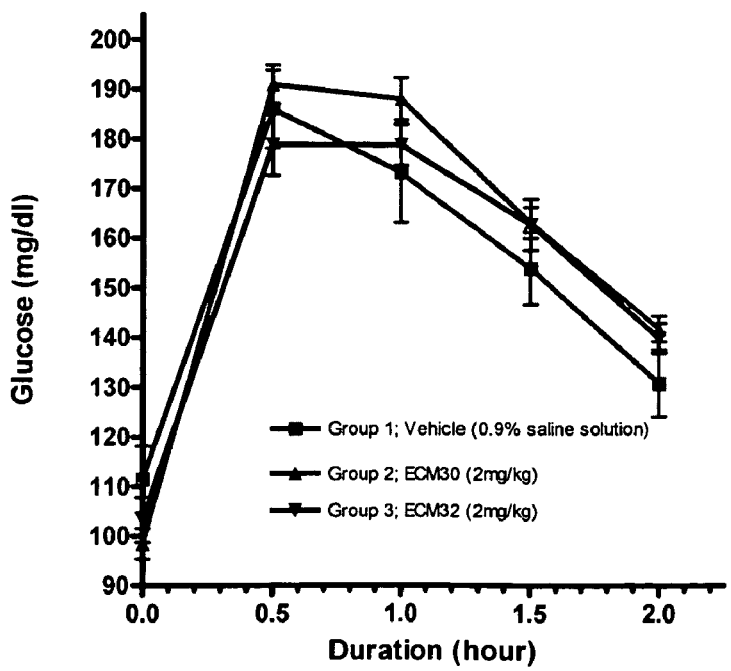
FIG. 2 is a plot of blood glucose levels in mg/dl as a function of time for a control, 2 mg/kg ECM30, and 2 mg/kg ECM32 in normal patients.

The peptides of SEQ ID NO:1 (ECM32) and SEQ ID NO:2 (ECM30) were tested by treating normal rat groups of 6 to 8 animals at 2 mg/mL in saline intravenously and compared to an untreated control group (0.9% saline solution only). All three groups were fasted on Day 0. Fasted plasma glucose and insulin were measured on Day 1 at 0, 30, 60, 90, and 120 minutes post glucose dose (5 mL/kg). Plasma levels of ECM30 and ECM32 were also measured. Plots of the data are shown in FIG. 1 and FIG. 2, for the insulin level in ng/mL and glucose level in mg/dL, respectively, as a function of time.

Both peptides of SEQ ID NO:1 (ECM32) and SEQ ID NO:2 (ECM30) showed marked elevation in the plasma insulin compared to the control group at several time points. For ECM30, the insulin peak was twice that observed for the control at the 30 minute time points. As all rats were normal (i.e., non-diabetic), the glucose peaked at 30 minutes at 175-210 mg/dl in all cases. It is reasoned that enough insulin was generated in the normal case to saturate the signaling. This supports that the peptide sequence of peptides of SEQ ID NO:1 (ECM32) and SEQ ID NO:2 (ECM30) or portions thereof can act as insulin-sensitizing agents.

Example 3

Plasma Glucose and Insulin Testing in Diabetic Rats

Figure 3:
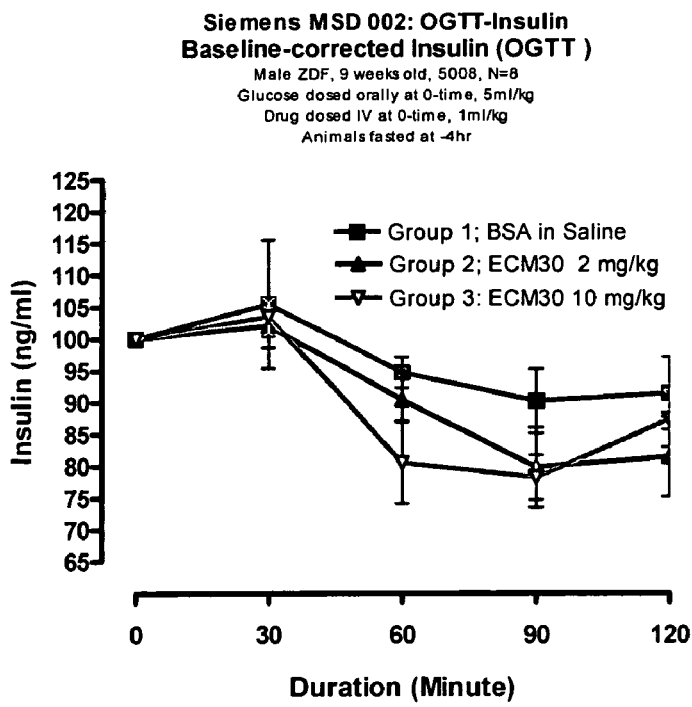
FIG. 3 is a plot of blood insulin levels in ng/ml as a function of time for a control (bovine serum albumin in saline), 2 mg/kg ECM30, and 10 mg/kg ECM30 in diabetic patients.
Figure 4:
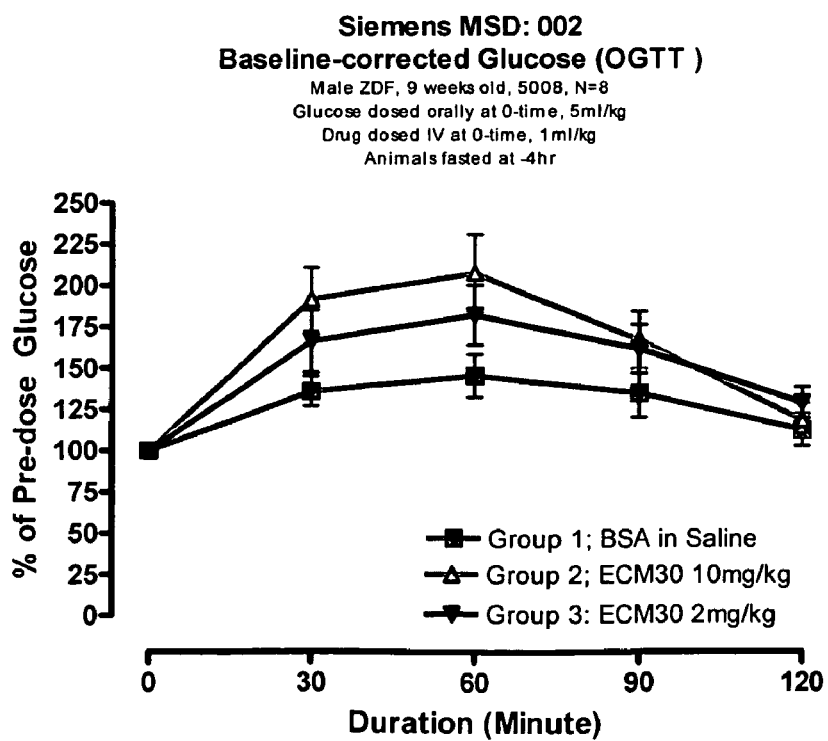
FIG. 4 is a plot of % of pre-dosed glucose as a function of time for a control (bovine serum albumin in saline), 2 mg/kg ECM30, and 10 mg/kg ECM30 in diabetic patients.

The peptide of SEQ ID NO:2 (ECM30) was tested by treating diabetic rat groups of 8 animals at 2 mg/mL and 10 mg/mL in saline intravenously and compared to a control group (bovine serum albumin in saline). All three groups were fasted on Day 0. Fasted plasma glucose and insulin were be measured on Day 1 at 0, 30, 60, 90, and 120 minutes post glucose dose. Plots of the data are shown in FIG. 3 and FIG. 4, for the insulin level and % of pre-dose glucose in ng/ml, respectively, as a function of time. ECM30 did not increase insulin.

Example 4

Cleavage Enzymes

The cleavage enzymes for ECM32 are also potential therapeutic targets. ECM32 sequence at the cleavage site was matched to Elastase (X-VV) and ADAM17 (X-VVAA) as potential enzymes (proteases) able to cleave or bind ECM32. The peptides of SEQ ID NO:1 (ECM32) and SEQ ID NO:2 (ECM30) were tested at levels of 0 mg/L, 12.5 mg/L, 25 mg/L, and 50 mg/L for their effect on cleavage enzymes.

Figure 5:
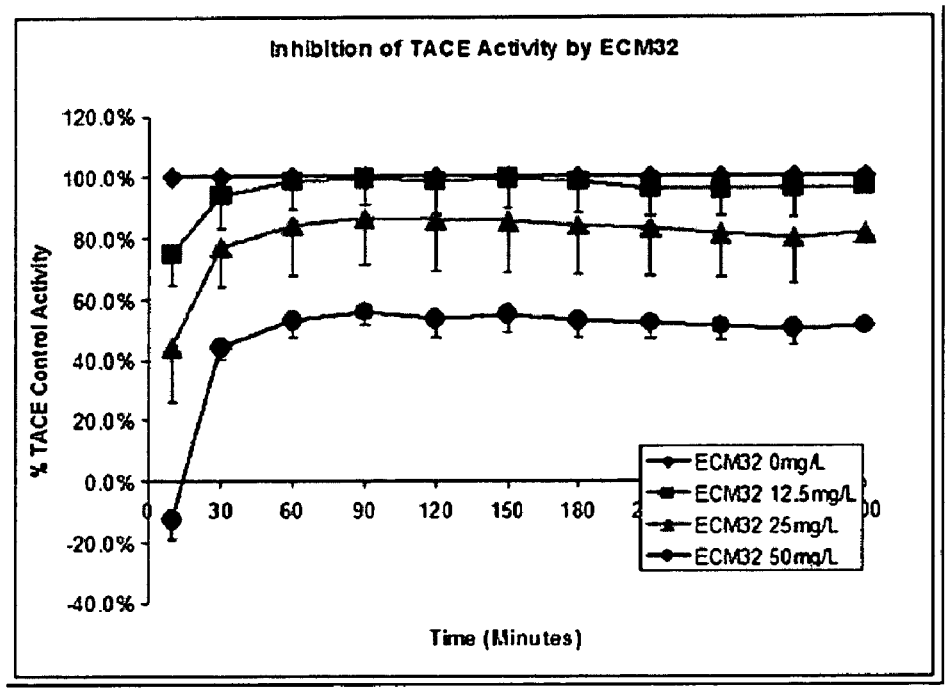
FIG. 5 is a plot of % TACE control activity as a function of time for ECM32 at levels of 0 mg/L, 12.5 mg/L, 25 mg/L, and 50 mg/L.
Figure 6:
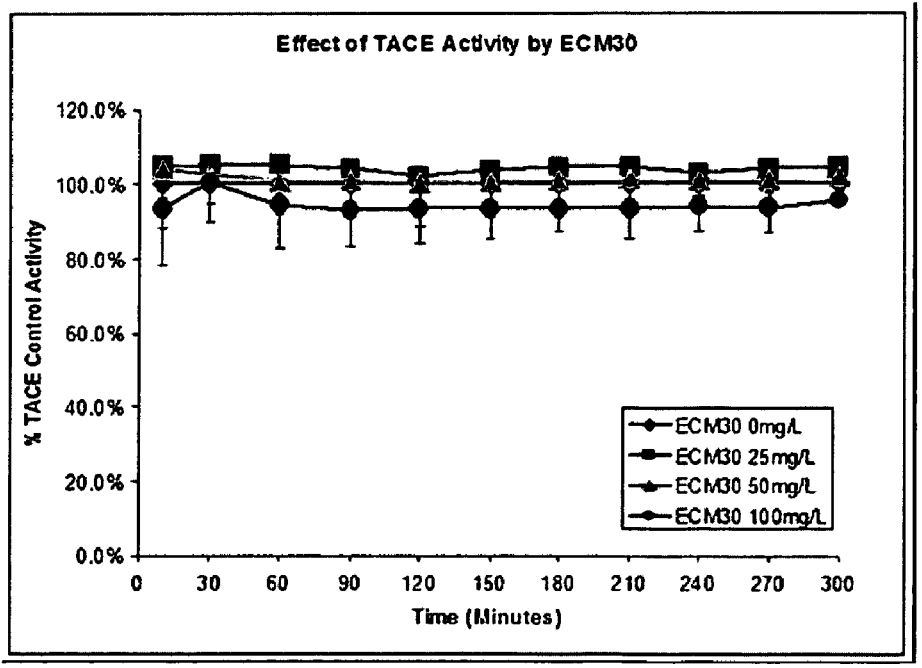
FIG. 6 is a plot of % TACE control activity as a function of time for ECM30 at levels of 0 mg/L, 12.5 mg/L, 25 mg/L, and 50 mg/L.

ECM32 was found to have a strong inhibitory effect on ADAM-17, as shown in FIG. 5. The uncleaved ECM30 did not significantly inhibit ADAM-17 activities, as shown in FIG. 6. Neither ECM30 nor ECM32 showed elastase inhibition. ECM30 and/or ECM32 are/is also potentially bound to IDE insulin degradation enzyme IDE (L-V) as inhibition of IDE was observed with ECM32. ADAM-17 and IDE both impact insulin concentration. This data shows that ECM32 has an inhibitory effect on several proteases affecting insulin concentrations. This data also shows ECM32 can be formed by several proteases.

ECM30 did not lack natural ECM32, but they had lower levels than normal rats. The ADAM-17 and IDE function in these rats could be altered leading to the disease state. Without wishing to be bound by theory, it is believed that IDE is not as inhibited by ECM30 in diabetic rats due to altered ADAM-17 activity.

Example 5

Effect of ECM32 Injection on Insulin Resistance

Figure 7:
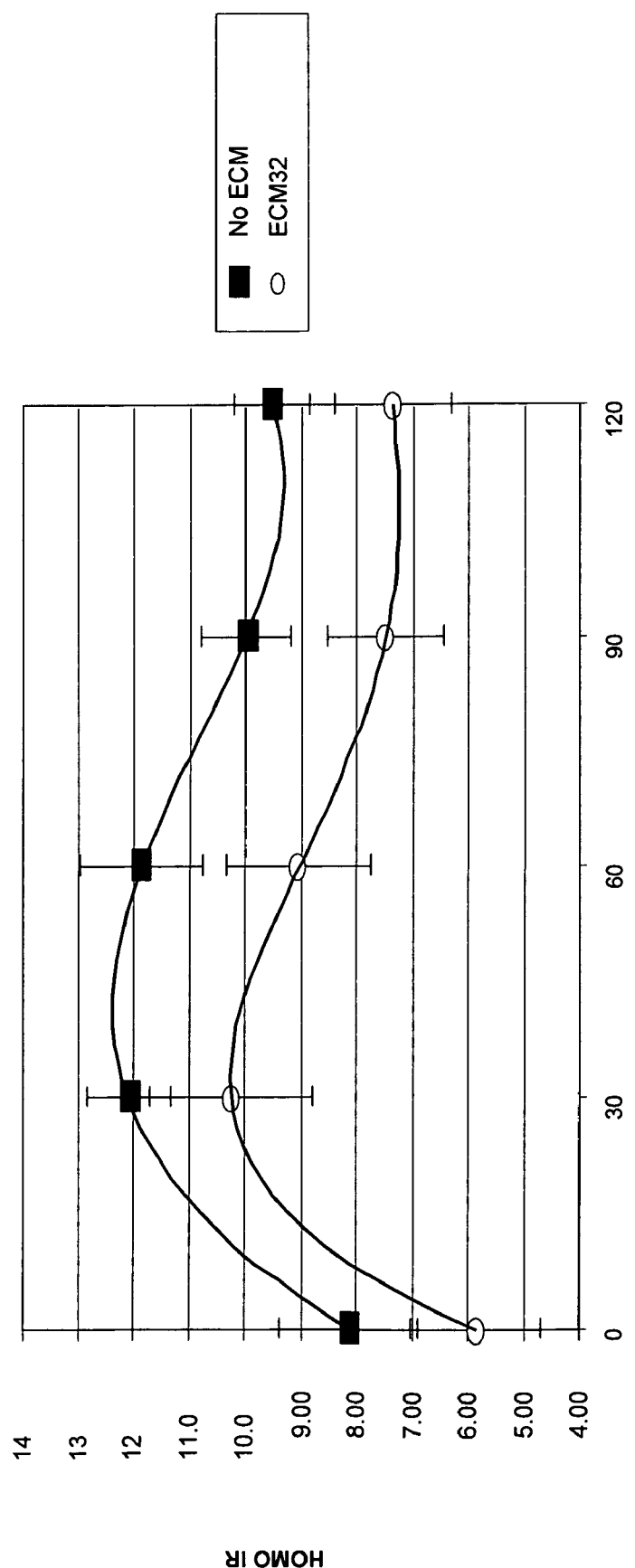
FIG. 7 is a homeostasis model assessment resistance (HOMO-IR) as a function of time (in minutes) for a control (no ECM32) and ECM32 (SEQ ID NO:1) administered via injection on the insulin resistance in glucose in diabetic rats.

The effect of ECM32 (SEQ ID NO:1) injection on the insulin resistance in glucose in diabetic rats was evaluated. The homeostasis model assessment resistance (HOMO-IR) results for ECM32 (SEQ ID NO:1) and control (no ECM32) are shown in FIG. 7.

Example 6

Effect on Plasma Glucose Level

Figure 8:
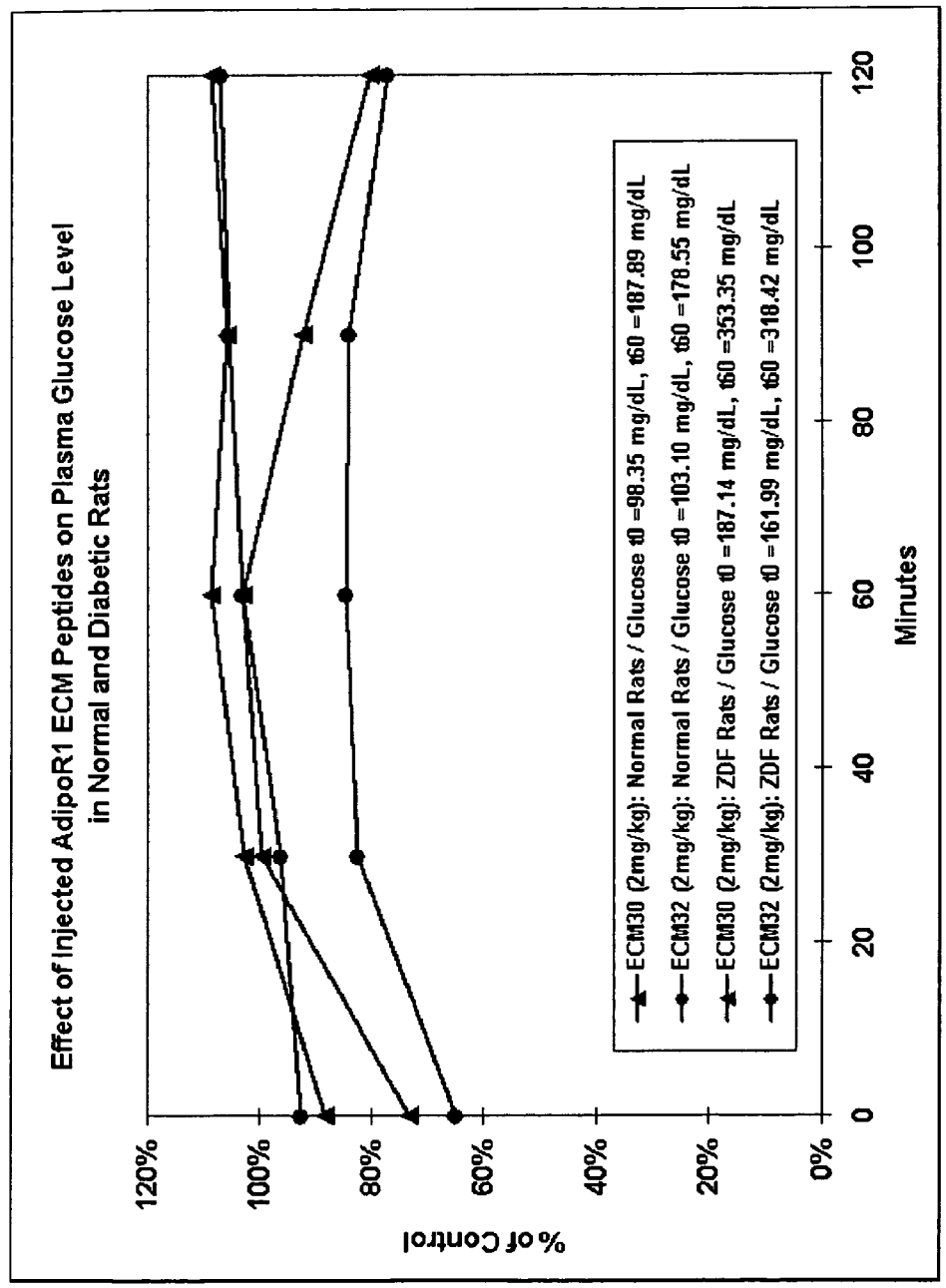
FIG. 8 is a plot of % of control as a function of time for ECM32 (SEQ ID NO:1) and ECM30 (SEQ ID NO:2) for plasma glucose levels in normal and diabetic rats.

The effect of ECM32 (SEQ ID NO:1) and ECM30 (SEQ ID NO:2) on the plasma glucose levels in normal and diabetic rats was evaluated. The peptides were injected at 2 mg/kg along with a control group. ECM32 lowered glucose levels, as would be expected by increased insulin. ECM30 also lowered glucose levels, but at longer time points. This could be due to ADAM-17 cleavage of ECM30 into IDE inhibitory forms in vivo. The results are shown in FIG. 8.

Example 7

Effect on Plasma Adiponectin and ECM32 Levels

The effect of ECM32 (SEQ ID NO:1) on the plasma adiponectin and ECM32 levels in normal and diabetic rats was evaluated. The peptide was injected at 2 mg/kg along with a control group. The results are shown in TABLE 2 below.

TABLE 2

| Mean ± SD | Adiponectin in Plasma (μg/ml) | | ECM32 (AdipoR1) in Plasma (ng/ml) | |
|---|---|---|---|---|
| | Control | ECM32 (2 mg/kg 120 min) | Control | ECM32 (2 mg/kg 120 min) |
| Normal Rats (SD) | 24.09 ± 3.72 | 20.00 ± 8.07 | 98.80 ± 22.95 | 112.94 ± 18.49 |
| Diabetic Rats (ZDF) | 20.85 ± 3.94 | 20.46 ± 3.41 | 63.66 ± 7.98 | 95.08 ± 36.13 |

Example 8

Inhibition of IDE Activity

Figure 9:
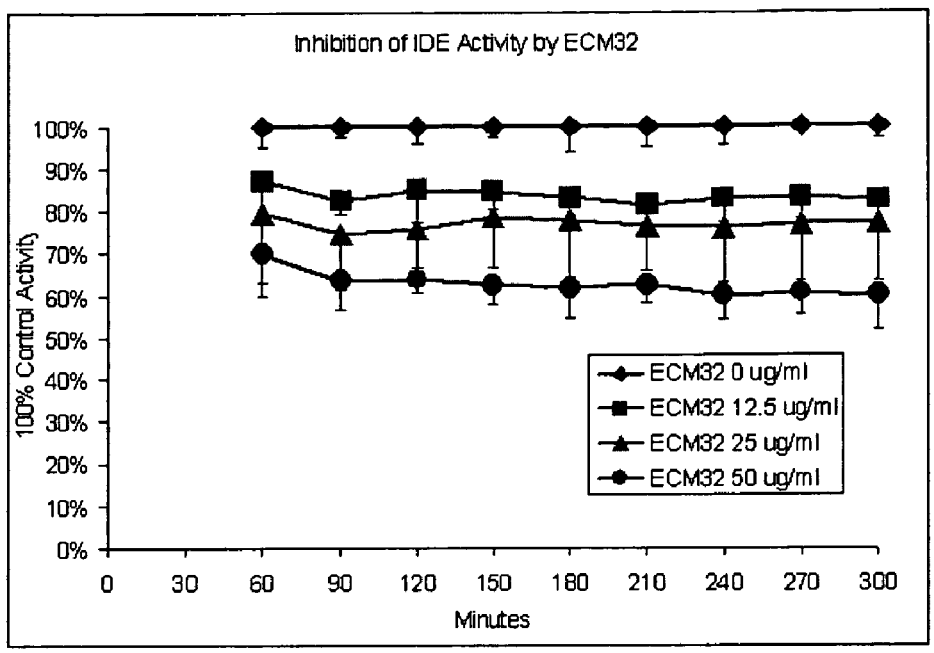
FIG. 9 is a plot of % of control as a function of time for the inhibition of IDE activity for ECM32 (SEQ ID NO:1) administered at four level (0, 12.5, 25, and 50 µg/ml).
Figure 10:
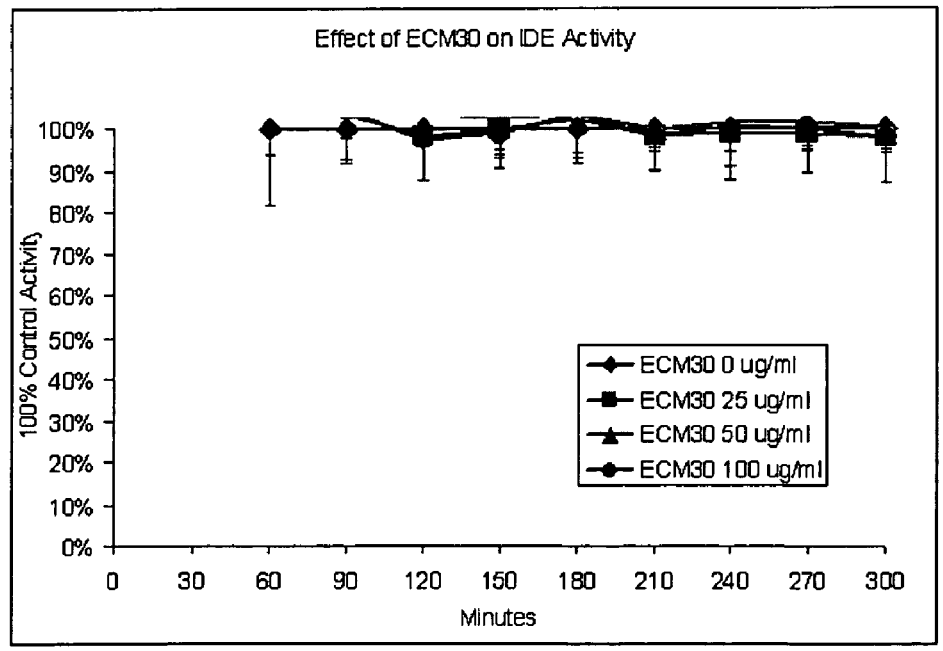
FIG. 10 is a plot of % of control as a function of time for the inhibition of IDE activity for ECM30 (SEQ ID NO:2) administered at four level (0, 25, 50, and 100 µg/ml).

The effect of ECM32 (SEQ ID NO:1) and ECM30 (SEQ ID NO:2) on IDE activity over time was evaluated at four different dose levels (0, 12.5, 25, and 50 μg/ml for ECM32 and 0, 25, 50, and 100 μg/ml for ECM30). The results are shown in FIG. 9 for ECM32 (SEQ ID NO:1) and FIG. 10 for ECM30 (SEQ ID NO:2). As can be seen from these figures, ECM32 inhibits IDE activity over time, but ECM30 has no significant effect on IDE over time.

Example 9

Inhibition of ADAM-17 Activity

The effect of ECM32 (SEQ ID NO:1), ECM30 (SEQ ID NO:2), ECM25 (SEQ ID NO:5), ECM10 (SEQ ID NO:6), ECM12 (SEQ ID NO:7), and ECM9 (SEQ ID NO:8) on ADAM-17 activity was evaluated. The results are shown in TABLE 3 below. As can be seen from the table, ECM32 (SEQ ID NO:1), ECM25 (SEQ ID NO:5), ECM10 (SEQ ID NO:6), ECM12 (SEQ ID NO:7), and ECM9 (SEQ ID NO:8) inhibit IDE activity, but ECM30 has no significant effect on IDE. As can also be seen from the table, ECM32 (SEQ ID NO:1) inhibits ADAM-17 activity, but ECM30 (SEQ ID NO:2), ECM25 (SEQ ID NO:5), ECM10 (SEQ ID NO:6), ECM12 (SEQ ID NO:7), and ECM9 (SEQ ID NO:8) have no significant effect on ADAM-17 activity.

TABLE 3

| Peptide | MALDI mass | ADAM 17 inhibition | IDE inhibition |
|---|---|---|---|
| ECM 30 (SEQ ID NO: 2) | 3284.6 | negative | negative |
| ECM 32 (SEQ ID NO: 1) | 3494.3 | positive | positive |
| ECM 25 (SEQ ID NO: 5) | — | negative | positive |
| ECM 10 (VY-10) VVAAAFVHFY (SEQ ID NO: 6) | 1123.3 | negative | positive |
| ECM12 (HR-12-3) HFYGVSNLQEFR (SEQ ID NO: 7) | 1496.6 | negative | positive |
| ECM 9 (SL-9-2) SGCTDDTLL (SEQ ID NO: 8) | 924.5 | negative | positive |

When ranges are used herein for physical properties, such as molecular weight, or chemical properties, such as chemical formulae, all combinations and subcombinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A method of treating diabetes in a patient in need thereof, comprising the step of:
   administering to said patient an effective amount of a peptide or a pharmaceutically-acceptable salt thereof;
   wherein said peptide has at least 75% identity with SEQ ID NO:1.

2. A method of claim 1,
   wherein said patient suffers from type I or type II diabetes.

3. A method of claim 1,
   wherein said patient suffers from gestational diabetes.

4. A method of claim 1,
   wherein said peptide has at least 80% identity with SEQ ID NO:1.

5. A method of claim 1,
   wherein said peptide has at least 90% identity with SEQ ID NO:1.

6. A method of claim 1,
   wherein said peptide has at least 95% identity with SEQ ID NO:1.

7. A method of claim 1,
   wherein said peptide has at least 97% identity with SEQ ID NO:1.

8. A method of claim 1,
   wherein said peptide has at least 98% identity with SEQ ID NO:1.

9. A method of treating abnormal adipocyte activity in a patient in need thereof, comprising the step of:

administering to said patient an effective amount of a peptide or a pharmaceutically-acceptable salt thereof;
wherein said peptide has at least 75% identity with SEQ ID NO:1.

10. A method of claim 9,
wherein said peptide has at least 80% identity with SEQ ID NO:1.

11. A method of claim 9,
wherein said peptide has at least 90% identity with SEQ ID NO:1.

12. A method of claim 9,
wherein said peptide has at least 95% identity with SEQ ID NO:1.

13. A method of claim 9,
wherein said peptide has at least 97% identity with SEQ ID NO:1.

14. A method of claim 9,
wherein said peptide has at least 98% identity with SEQ ID NO:1.

15. A method of treating insulin resistance in a patient in need thereof, comprising the step of:
administering to said patient an effective amount of a peptide or a pharmaceutically-acceptable salt thereof;
wherein said peptide has at least 75% identity with SEQ ID NO:1.

16. A method of claim 15,
wherein said peptide has at least 90% identity with SEQ ID NO:1.

17. A method of claim 15,
wherein said peptide has at least 95% identity with SEQ ID NO:1.

18. A method of claim 15,
wherein said peptide has at least 97% identity with SEQ ID NO:1.

19. A method of claim 15,
wherein said peptide has at least 98% identity with SEQ ID NO:1.

20. A method of treating metabolic syndrome in a patient in need thereof, comprising the step of:
administering to said patient an effective amount of a peptide or a pharmaceutically-acceptable salt thereof;
wherein said peptide has at least 75% identity with SEQ ID NO:1.

21. A method of claim 20,
wherein said peptide has at least 90% identity with SEQ ID NO:1.

22. A method of claim 20,
wherein said peptide has at least 95% identity with SEQ ID NO:1.

23. A method of claim 20,
wherein said peptide has at least 97% identity with SEQ ID NO:1.

24. A method of claim 20,
wherein said peptide has at least 98% identity with SEQ ID NO:1.

25. A method of causing insulin secretion in a patient, comprising the step of:
administering to said patient an effective amount of a peptide or a pharmaceutically-acceptable salt thereof;
wherein said peptide has at least 75% identity with SEQ ID NO:1;
wherein said patient suffers from diabetes.

26. A method of causing insulin secretion in a patient, comprising the step of:
administering to said patient an effective amount of a peptide or a pharmaceutically-acceptable salt thereof;
wherein said peptide has at least 75% identity with SEQ ID NO:1;
wherein said patient suffers from abnormal adipocyte activity.

27. A method of causing insulin secretion in a patient, comprising the step of:
administering to said patient an effective amount of a peptide or a pharmaceutically-acceptable salt thereof;
wherein said peptide has at least 75% identity with SEQ ID NO:1;
wherein said patient suffers from insulin resistance.

28. A method of causing insulin secretion in a patient, comprising the step of:
administering to said patient an effective amount of a peptide or a pharmaceutically-acceptable salt thereof;
wherein said peptide has at least 75% identity with SEQ ID NO:1;
wherein said patient suffers from metabolic syndrome.

* * * * *